United States Patent
Dhau et al.

(10) Patent No.: US 12,251,481 B2
(45) Date of Patent: Mar. 18, 2025

(54) PHOTOCATALYTIC FLUID FILTRATION SYSTEM AND METHOD

(71) Applicant: Molekule Group, Inc., San Francisco, CA (US)

(72) Inventors: Jaspreet S. Dhau, San Francisco, CA (US); Dilip N. Goswami, San Francisco, CA (US); Philip Myers, San Francisco, CA (US); David Sanabria, San Francisco, CA (US); Rick C. Rasor, San Francisco, CA (US)

(73) Assignee: Molekule, Inc., San Francisco, CA (US)

( * ) Notice: Subject to any disclaimer, the term of this patent is extended or adjusted under 35 U.S.C. 154(b) by 732 days.

(21) Appl. No.: 17/340,793

(22) Filed: Jun. 7, 2021

(65) Prior Publication Data
US 2021/0379220 A1    Dec. 9, 2021

Related U.S. Application Data

(60) Provisional application No. 63/035,637, filed on Jun. 5, 2020.

(51) Int. Cl.
A61L 2/10    (2006.01)
A61L 9/20    (2006.01)
(Continued)

(52) U.S. Cl.
CPC .............. *A61L 2/10* (2013.01); *A61L 9/205* (2013.01); *B01D 39/10* (2013.01);
(Continued)

(58) Field of Classification Search
CPC ........ A61L 2/10; A61L 9/205; A61L 2202/11; A61L 9/18; A61L 9/20; A61L 2209/14;
(Continued)

(56) References Cited

U.S. PATENT DOCUMENTS

| 933,702 A | 9/1909 | Fowden |
| 4,065,276 A | 12/1977 | Nakaya et al. |

(Continued)

FOREIGN PATENT DOCUMENTS

| CA | 3095953 A1 | 10/2019 |
| CN | 204730343 U | 10/2015 |

(Continued)

OTHER PUBLICATIONS

Samburova, Vera , et al., "Dominant volatile organic compounds (VOCs) measured at four Cannabis growing facilities: Pilot study results", Journal of the Air & Waste Management Association, Sep. 9, 2019.

(Continued)

*Primary Examiner* — Sean E Conley
*Assistant Examiner* — Brendan A Hensel
(74) *Attorney, Agent, or Firm* — Jeffrey Schox; Randy Mehlenbacher

(57) ABSTRACT

A fluid purification system can include a filter comprising photocatalytic material, a light source configured to illuminate the photocatalytic material, and a scattering film configured to scatter light emitted from the light source.

6 Claims, 9 Drawing Sheets

(51) Int. Cl.
*B01D 39/10* (2006.01)
*B82Y 30/00* (2011.01)

(52) U.S. Cl.
CPC ........ *A61L 2202/11* (2013.01); *A61L 2209/14* (2013.01); *B01D 2201/0415* (2013.01); *B01D 2201/12* (2013.01); *B82Y 30/00* (2013.01)

(58) Field of Classification Search
CPC ............ B01D 39/10; B01D 2201/0415; B01D 2201/12; B01D 2257/708; B01D 2257/91; B01D 2259/804; B01D 46/0027; B01D 46/521; B01D 53/885; B82Y 30/00
See application file for complete search history.

(56) References Cited

U.S. PATENT DOCUMENTS

| | | |
|---|---|---|
| 4,896,590 A | 1/1990 | Groos |
| 4,931,654 A | 6/1990 | Horng |
| D328,946 S | 8/1992 | Havrilla |
| D360,635 S | 7/1995 | Mark |
| D362,441 S | 9/1995 | Mark |
| 5,453,049 A | 9/1995 | Tillman et al. |
| 5,505,904 A | 4/1996 | Haidinger et al. |
| 5,620,669 A | 4/1997 | Plinke et al. |
| 5,790,934 A | 8/1998 | Say et al. |
| D400,663 S | 11/1998 | Furlough |
| 5,873,920 A | 2/1999 | Wong et al. |
| 5,922,093 A | 7/1999 | James et al. |
| 5,933,702 A | 8/1999 | Goswami |
| 6,531,100 B1 | 3/2003 | Ogata et al. |
| 6,607,702 B1 | 8/2003 | Kang et al. |
| 6,613,277 B1 | 9/2003 | Monagan |
| D493,874 S | 8/2004 | Woods |
| D505,999 S | 6/2005 | Song |
| 6,939,397 B2 | 9/2005 | Nelsen et al. |
| 7,063,820 B2 | 6/2006 | Goswami |
| 7,074,369 B2 | 7/2006 | Tabatabaie-Raissi et al. |
| 7,160,506 B2 | 1/2007 | Deshpande |
| D552,724 S | 10/2007 | Chen |
| 7,291,205 B2 | 11/2007 | Chu |
| 7,371,351 B2 | 5/2008 | Goswami |
| 7,566,359 B2 | 7/2009 | Goel et al. |
| D611,579 S | 3/2010 | Zlotnik et al. |
| 7,820,100 B2 | 10/2010 | Garfield et al. |
| 7,910,940 B2 | 3/2011 | Koike et al. |
| 8,003,058 B2 | 8/2011 | Bergeron et al. |
| D648,429 S | 11/2011 | Choi et al. |
| D652,408 S | 1/2012 | Chen |
| D687,017 S | 7/2013 | Ashcraft et al. |
| D697,496 S | 1/2014 | Ashcraft et al. |
| 8,658,046 B2 | 2/2014 | Barry et al. |
| 8,709,341 B2 | 4/2014 | Day et al. |
| D710,329 S | 8/2014 | Holzer |
| D716,427 S | 10/2014 | Lim et al. |
| D717,420 S | 11/2014 | Von Seggern |
| D744,541 S | 12/2015 | Langhammer et al. |
| D752,732 S | 3/2016 | Ansley et al. |
| D754,832 S | 4/2016 | Seo et al. |
| D766,213 S | 9/2016 | Hinokio |
| D768,844 S | 10/2016 | Koseoglu et al. |
| D773,704 S | 12/2016 | Pardo et al. |
| D774,020 S | 12/2016 | Hinokio |
| 9,662,626 B2 | 5/2017 | Yates et al. |
| D796,019 S | 8/2017 | Thompson |
| D802,022 S | 11/2017 | Yao et al. |
| D803,369 S | 11/2017 | Kim et al. |
| D803,810 S | 11/2017 | Lee et al. |
| D804,002 S | 11/2017 | Huang |
| D805,622 S | 12/2017 | Lee |
| D806,843 S | 1/2018 | Mcdonnell |
| D807,327 S | 1/2018 | Xiong |
| D808,927 S | 1/2018 | Schaal et al. |
| D810,049 S | 2/2018 | Lee et al. |
| D810,135 S | 2/2018 | Langhammer et al. |
| D810,137 S | 2/2018 | Tsang et al. |
| D810,265 S | 2/2018 | Chen |
| D810,266 S | 2/2018 | Li |
| D818,097 S | 5/2018 | Cho et al. |
| 10,039,852 B2 | 8/2018 | Yi et al. |
| D828,912 S | 9/2018 | Powell et al. |
| D829,312 S | 9/2018 | Riering-Czekalla et al. |
| D829,314 S | 9/2018 | Cho et al. |
| D831,810 S | 10/2018 | Cho et al. |
| D831,811 S | 10/2018 | Cho et al. |
| D832,414 S | 10/2018 | Sharma et al. |
| 10,105,463 B2 | 10/2018 | Kim et al. |
| D834,694 S | 11/2018 | Walter et al. |
| 10,137,216 B2 | 11/2018 | Goswami et al. |
| D835,766 S | 12/2018 | Chen |
| D836,760 S | 12/2018 | Fredäng et al. |
| 10,183,187 B2 | 1/2019 | Li |
| 10,517,980 B2 | 12/2019 | Kim et al. |
| 10,684,027 B2 | 6/2020 | Goswami et al. |
| 10,933,159 B2 | 3/2021 | Benedek et al. |
| 10,981,102 B2 | 4/2021 | Trent et al. |
| 2002/0160913 A1 | 10/2002 | Sangiovanni et al. |
| 2003/0180200 A1 | 9/2003 | Reisfeld |
| 2004/0007000 A1 | 1/2004 | Takeda et al. |
| 2004/0013583 A1 | 1/2004 | Burkhardt |
| 2004/0146437 A1 | 7/2004 | Arts et al. |
| 2004/0166037 A1 | 8/2004 | Youdell et al. |
| 2005/0061656 A1 | 3/2005 | Benoit et al. |
| 2005/0129591 A1 | 6/2005 | Wei et al. |
| 2005/0138905 A1 | 6/2005 | Kubokawa |
| 2005/0201907 A1 | 9/2005 | Wakamura |
| 2006/0057020 A1 | 3/2006 | Tufo |
| 2006/0124442 A1 | 6/2006 | Valpey et al. |
| 2006/0150818 A1 | 7/2006 | Okamoto et al. |
| 2006/0188388 A1 | 8/2006 | Goswami |
| 2007/0059225 A1 | 3/2007 | Willette |
| 2007/0199288 A1 | 8/2007 | Paterson et al. |
| 2007/0213002 A1 | 9/2007 | Okamoto et al. |
| 2007/0253860 A1 | 11/2007 | Schroder |
| 2008/0050288 A1 | 2/2008 | Okamoto et al. |
| 2008/0112845 A1 | 5/2008 | Dunn et al. |
| 2009/0002985 A1 | 1/2009 | Peck et al. |
| 2009/0032390 A1 | 2/2009 | Osterlund |
| 2009/0175757 A1 | 7/2009 | Yao et al. |
| 2009/0229478 A1 | 9/2009 | Wu |
| 2009/0245594 A1 | 10/2009 | Abramovich et al. |
| 2010/0003164 A1 | 1/2010 | Bourne et al. |
| 2010/0101413 A1 | 4/2010 | Jones et al. |
| 2010/0143205 A1 | 6/2010 | Engelhard |
| 2010/0196222 A1 | 8/2010 | Kosugi et al. |
| 2010/0196223 A1 | 8/2010 | Hay et al. |
| 2010/0260644 A1 | 10/2010 | Day et al. |
| 2010/0303678 A1 | 12/2010 | Lockhart et al. |
| 2011/0088375 A1 | 4/2011 | Suzuki et al. |
| 2011/0101712 A1 | 5/2011 | Laconte |
| 2011/0117002 A1 | 5/2011 | Dardas et al. |
| 2011/0203238 A1 | 8/2011 | Witter et al. |
| 2012/0063958 A1 | 3/2012 | Riviere et al. |
| 2012/0183443 A1 | 7/2012 | Hurley |
| 2012/0199005 A1 | 8/2012 | Koji et al. |
| 2012/0273340 A1 | 11/2012 | Felix |
| 2013/0036908 A1 | 2/2013 | Jones et al. |
| 2013/0294968 A1 | 11/2013 | Owen et al. |
| 2014/0290489 A1 | 10/2014 | Jemura et al. |
| 2015/0008014 A1 | 1/2015 | Zhou et al. |
| 2015/0125355 A1 | 5/2015 | Lee et al. |
| 2015/0306271 A1 | 10/2015 | Willette |
| 2015/0320900 A1 | 11/2015 | Goswami et al. |
| 2015/0375187 A1 | 12/2015 | Yates et al. |
| 2016/0236129 A1 | 8/2016 | Ajemian |
| 2016/0279556 A1 | 9/2016 | Law |
| 2017/0043044 A1 | 2/2017 | Sobhy |
| 2017/0106218 A1 | 4/2017 | Lin et al. |
| 2017/0122605 A1 | 5/2017 | Lee et al. |
| 2017/0321717 A1 | 11/2017 | Park et al. |
| 2018/0027809 A1 | 2/2018 | Chiattello et al. |
| 2018/0117511 A1 | 5/2018 | Yamauchi et al. |
| 2018/0339073 A1 | 11/2018 | Clynne et al. |
| 2018/0344890 A1 | 12/2018 | Watanabe et al. |

(56) References Cited

U.S. PATENT DOCUMENTS

| | | |
|---|---|---|
| 2019/0063763 A1 | 2/2019 | Kleinberger et al. |
| 2019/0083674 A1 | 3/2019 | Jeong et al. |
| 2019/0083930 A1 | 3/2019 | Bernardoni et al. |
| 2019/0113246 A1 | 4/2019 | Goswami et al. |
| 2019/0120508 A1* | 4/2019 | Goswami ............ F24F 8/80 |
| 2020/0030731 A1 | 1/2020 | Dhau et al. |
| 2020/0061231 A1 | 2/2020 | Jeong et al. |
| 2020/0109869 A1 | 4/2020 | Mäkipääet al. |
| 2020/0129972 A1 | 4/2020 | Ozaki et al. |
| 2020/0182495 A1 | 6/2020 | Park et al. |
| 2020/0360858 A1 | 11/2020 | Mathur et al. |
| 2021/0100924 A1 | 4/2021 | Li et al. |
| 2021/0222897 A1 | 7/2021 | Sanabria et al. |
| 2021/0379220 A1 | 12/2021 | Dhau et al. |
| 2022/0032225 A1 | 2/2022 | Kim et al. |
| 2022/0062822 A1 | 3/2022 | Dhau et al. |

FOREIGN PATENT DOCUMENTS

| | | |
|---|---|---|
| CN | 106039994 A | 10/2016 |
| CN | 109078493 A | 12/2018 |
| JP | 2016084946 A | 5/2016 |
| JP | 2017148484 A | 8/2017 |
| KR | 20180057394 A | 5/2018 |
| KR | 101977573 B1 | 5/2019 |
| WO | 2004078320 A1 | 9/2004 |

OTHER PUBLICATIONS

Molekule Air Purifier found online—[Feb. 22, 2018]—https://molekule.com/?utm_source=google_search_s earch&utm_medium=rt&utm_campaign=brand&utm_term=term=molekule&utm_content=bmm_2&gclid=EAalQobChMI5ufdtbK62QIViYjICh3d8gvEAYAA SAAEgJcdPD_BwE.

International Search Report and Written Opinion for PCT Application No. PCT/US18/56061 mailed Jan. 4, 2019.

International Search Report and Written Opinion for PCT Application No. PCT/US2019/043804 mailed Dec. 2, 2019.

Molekule Website Screen Capture from Jun. 10, 2016 by Wayback Machine, (Year: 2016).

Molekule website screen grabs from Wayback Machine Internet Archive. Jun. 10, 2016 (Year: 2016).

Ochiai, Tsuyoshi , et al., Photoelectrochemical properties of TiO2 photocatalyst and its applications for environmental purification, Journal of Photochemistry and Photobiology C: Photochemistry reviews 13.4 (Dec. 1, 2012): 247-262.

Curtis, Gannon L., et al., "Reduction of Total and Viable Air Particles in the OR Setting by using Ultraviolet In-room Air Disinfection and Recirculation Units", American Association of Hip and Knee Surgeons, Cleveland Clinic, Nov. 4, 2017.

Hou, Wenbo , et al., A review of surface plasmon resonance-enhanced photocatalysis, Advanced 4, 15 Functional Materials 23.13 (Apr. 5, 2013): 1612-1619. p. 1 col. 2 para 1, p. 2 col. 1 para 2.

* cited by examiner

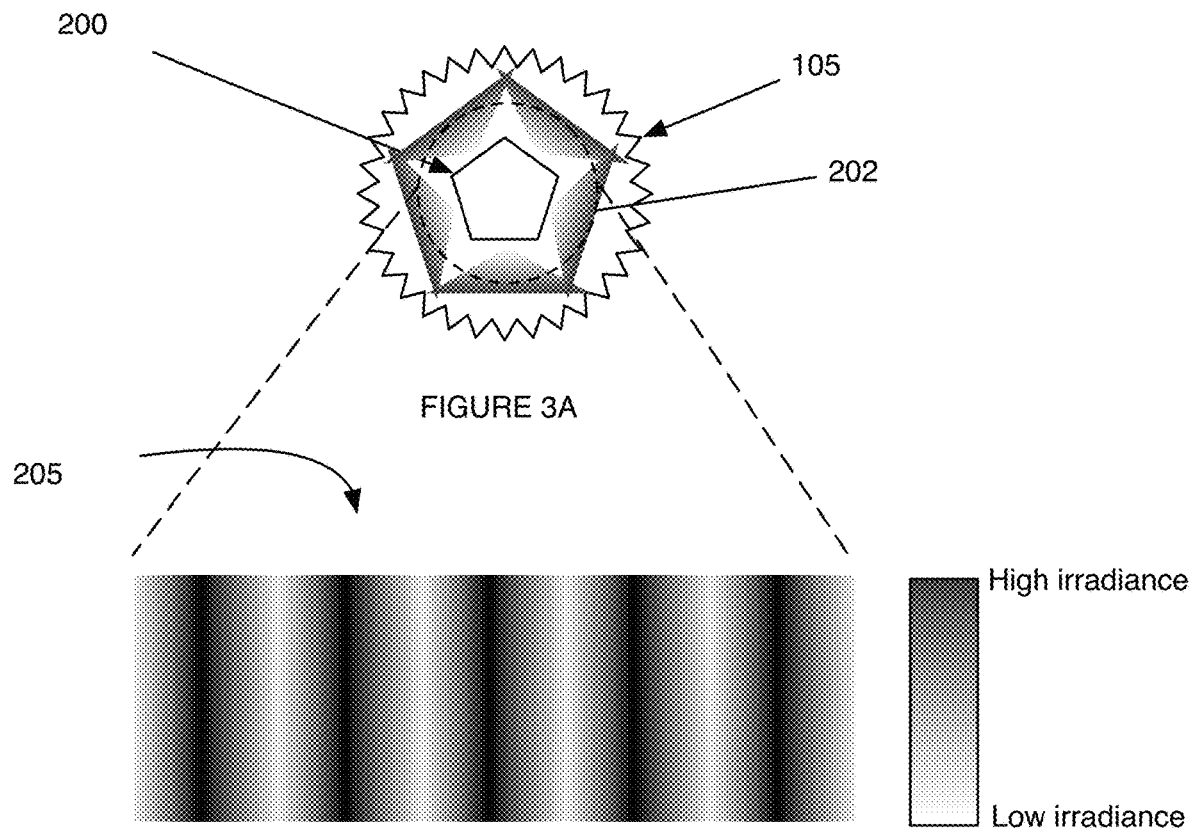
FIGURE 3A
FIGURE 3B
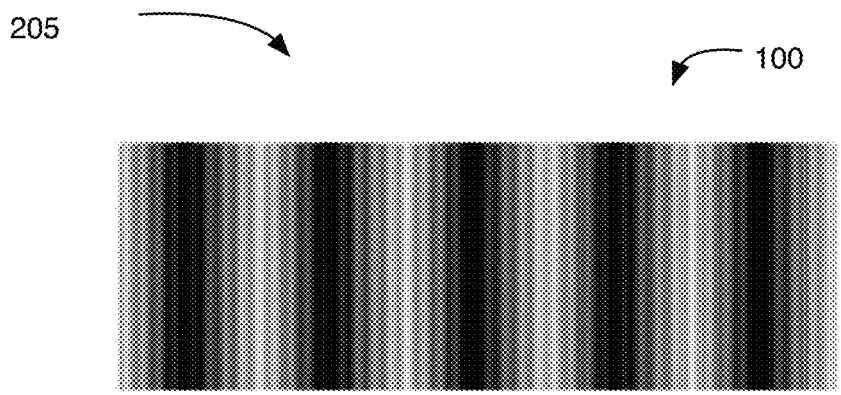
FIGURE 3C

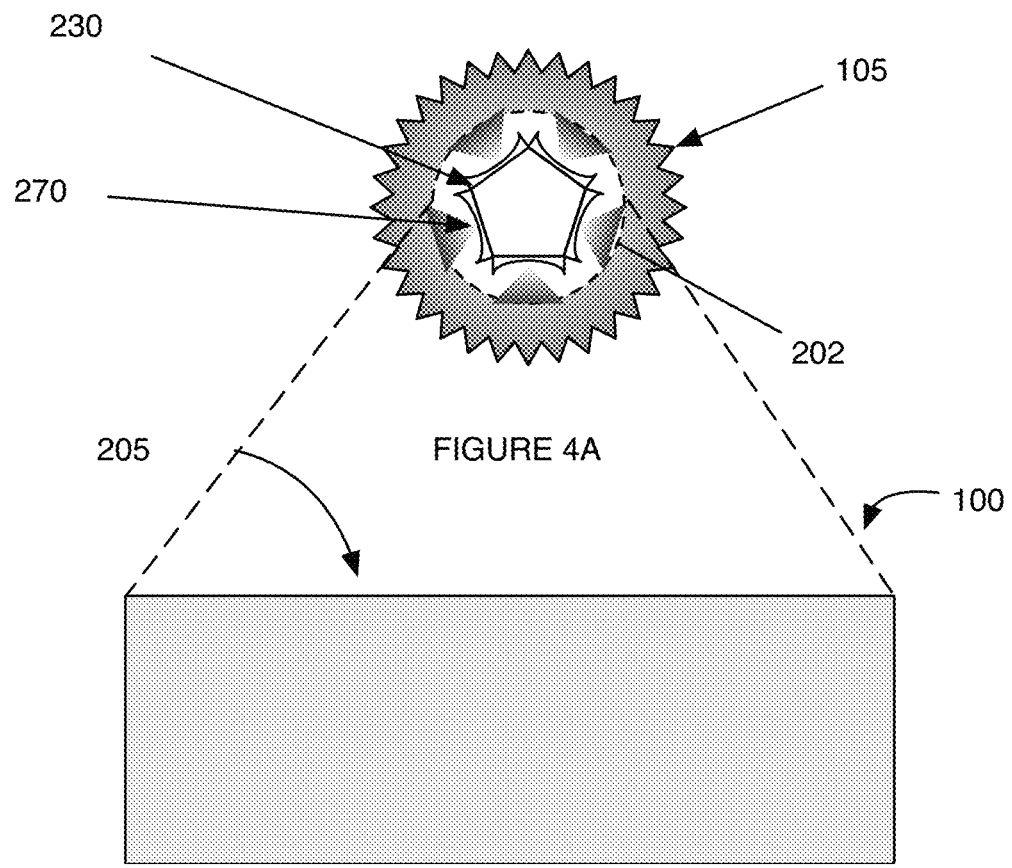
FIGURE 4A
FIGURE 4B
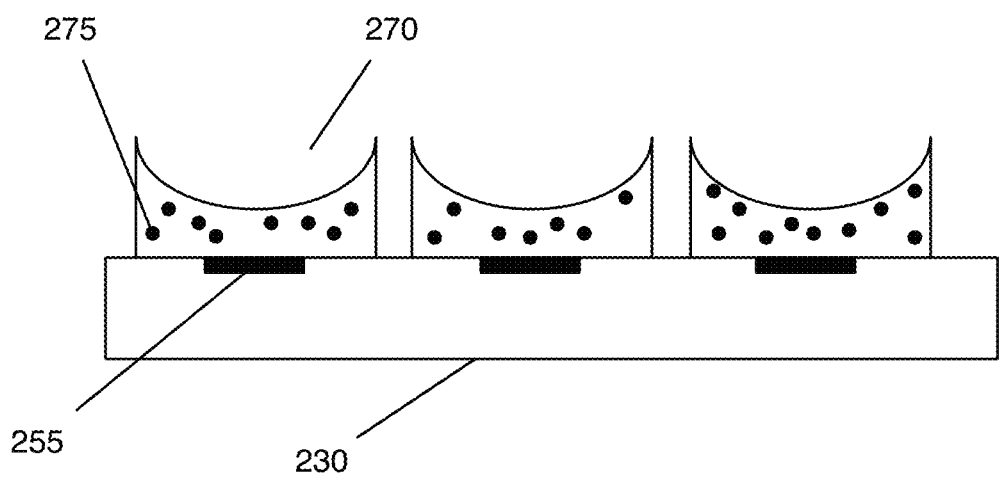
FIGURE 5A

PHOTOCATALYTIC FLUID FILTRATION SYSTEM AND METHOD

CROSS-REFERENCE TO RELATED APPLICATIONS

This application claims the benefit of U.S. Provisional Application No. 63/035,637, filed 5 Jun. 2020, which is incorporated in its entirety by this reference.

TECHNICAL FIELD

This invention relates generally to the photocatalysis field, and more specifically to a new and useful system and method in the photocatalysis field.

BACKGROUND

Many light sources produce hot and cold spots (e.g., uneven optical radiation distributions). In some applications, it can be beneficial to generate more even illumination. Thus, there is a need in the photocatalysis field for a new system and method. This invention provides such a new and useful system and method.

BRIEF DESCRIPTION OF THE FIGURES

FIG. 3A is a schematic representation of a top view of an embodiment of an optical assembly illuminating a filter.

FIGS. 3B and 3D are schematic representations of exemplar light intensity distributions produced by an optical assembly as shown in FIG. 3A at a location such as indicated by the dashed circle in FIG. 3A.

FIGS. 3C and 3E are a schematic representations of exemplary light intensity distributions at a filter face corresponding to the embodiment of the optical assembly in FIG. 3A.

FIG. 4A is a schematic representation of an embodiment of an optical assembly illuminating a filter.

FIG. 4B is a schematic representation of an example irradiance distribution at a filter face corresponding to the embodiment of the optical assembly in FIG. 4A.

FIGS. 5A, 5B, and 5C are schematic representations of embodiments of an optical assembly.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview.

Figure 1:
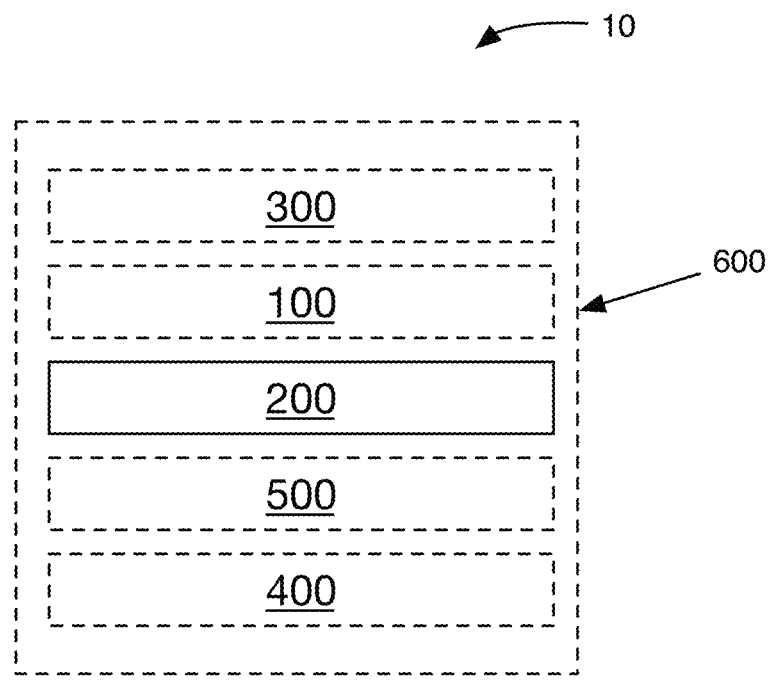
FIG. 1 is a schematic representation of the system.

As shown in FIG. 1, the system 10 can include an optical assembly 200, which functions to induce a substantially uniform irradiance pattern on an incident surface (e.g., air filter). The system can additionally or alternatively include at least one: housing 600, flow control mechanism 300, filter 100, sensor 500, computing system 400, and/or any suitable component. The optical assembly can include: a support structure 230, a light emitter 250, an optical device 270, a thermal management system, and/or any suitable component.

Figure 6A:
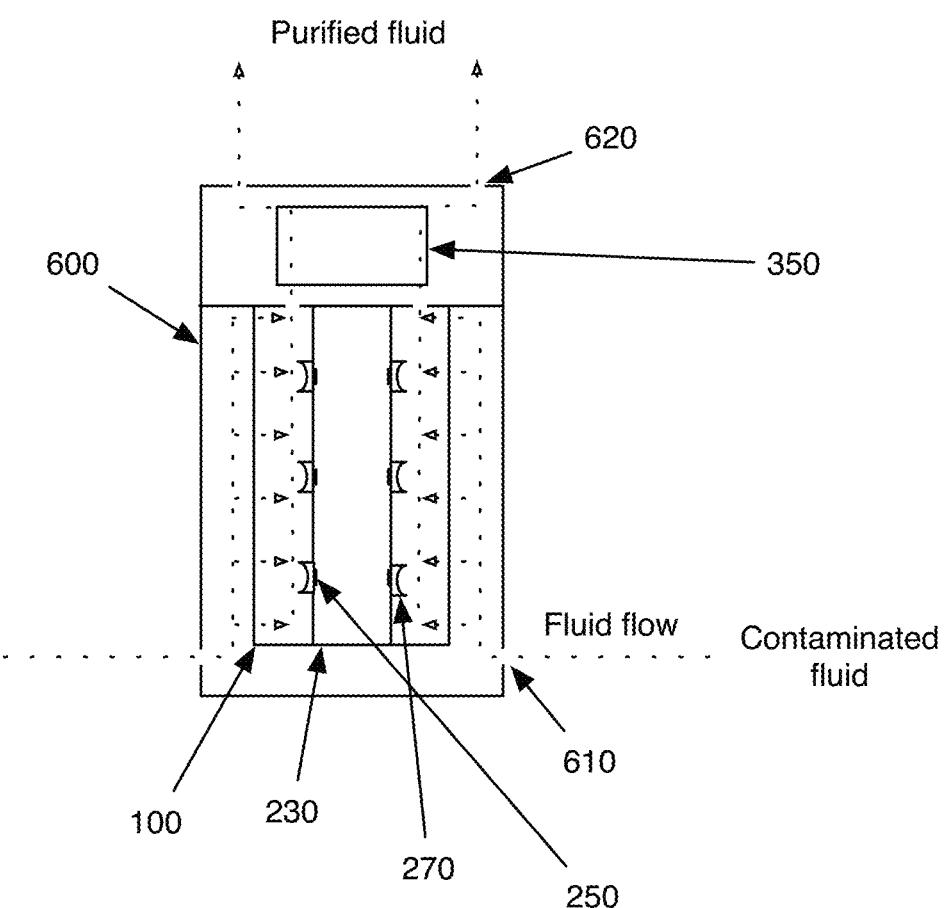
FIGS. 6A and 6B are schematic representations of examples of an air purification including an optical assembly.
Figure 6B:
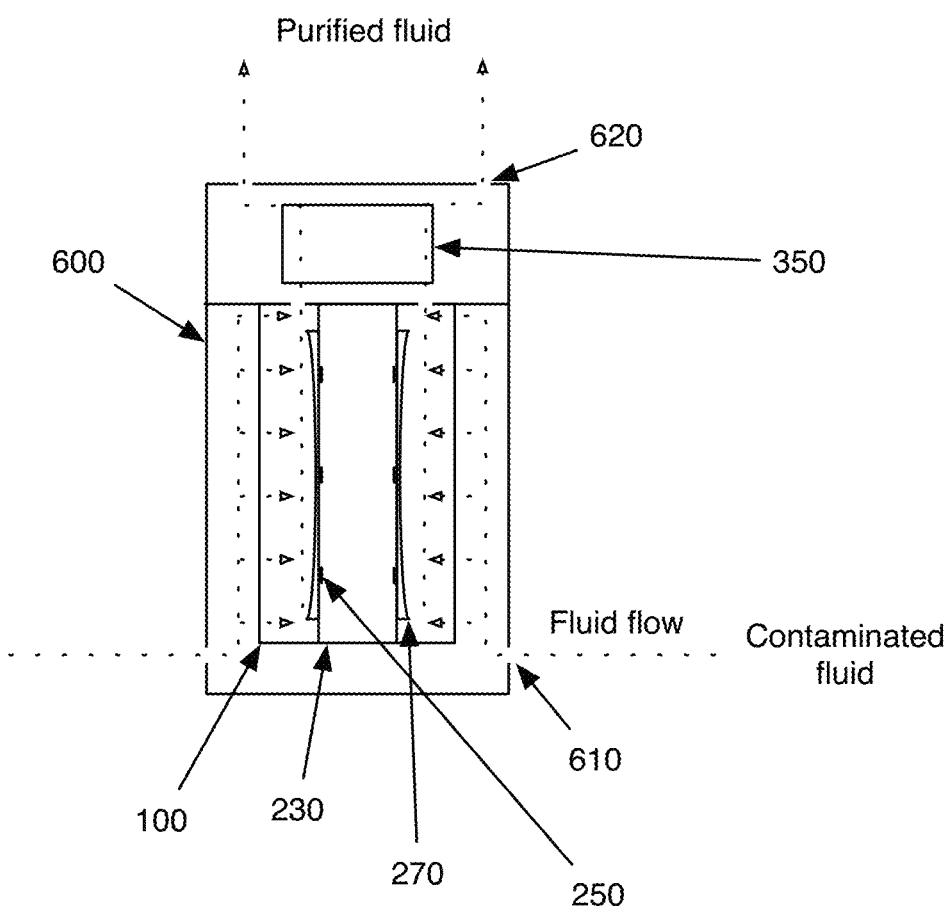
Figure 7A:
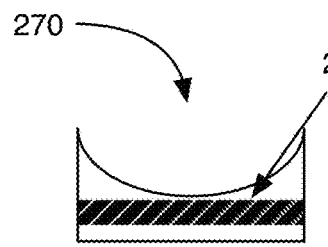
FIGS. 7A-7E are schematic representations of examples of patterning scattering sites within an optical material.
Figure 7B:
Figure 7C:
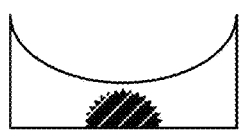
Figure 7D:
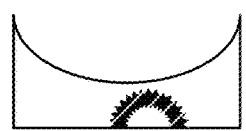
Figure 7E:
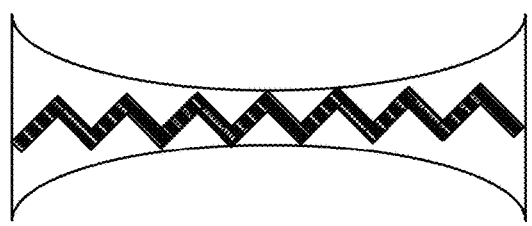
Figure 8A:
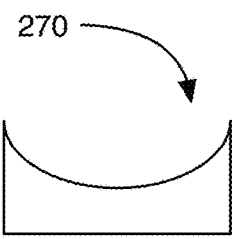
FIGS. 8A-8E are schematic representations of examples of different lens geometries.
Figure 8B:
Figure 8C:
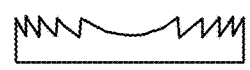
Figure 8D:
Figure 8E:
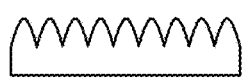

As shown schematically in FIG. 6A or 6B, the method can include providing a contaminated fluid, activating a material, degrading contaminants proximal to the activated material, and expelling purified fluid.

The system and method preferably function to remove (e.g., destroy) one or more contaminants from a fluid (e.g., liquid, gas, air, etc.). Contaminants can include volatile organic compounds (VOCs, such as terpenes, aromatic compounds, aliphatic compounds, etc.), particulate matter (e.g., microparticles, mesoparticles, macroparticles, nanoparticles, etc.), organic matter (e.g., pollen, mold, spores, bacteria, viruses, etc.), inorganic matter (e.g., nitrogen oxides ($NO_x$), sulfur oxides ($SO_x$), etc.), allergens (e.g., pet fur, dander, dust, etc.), and/or any suitable contaminants. Contaminants are preferably oxidized (e.g., to produce byproducts such as $CO_2$, $H_2O$, etc.), but may be reduced, and/or otherwise removed. Contaminants are preferably irreversibly removed from the fluid (e.g., not retained within a system, not able to return to an ambient environment, etc.), but can be reversibly removed (e.g., trapped, entrained, adsorbed). However, the system and/or method can additionally or alternatively be used generating more uniform light illumination in any suitable application.

2. Benefits.

Variations of the technology can confer several benefits and/or advantages.

First, the inventors have identified that many fluid filtration systems that use optical radiation (e.g., light) to degrade contaminants (e.g., directly such as UV-degradation, indirectly such as using photocatalytic processes, etc.) have 'hot spots' (e.g., local maxima) and 'cold spots' (e.g., local minima) in the irradiance distribution of the optical radiation (for example as shown in FIGS. 3A-3E). In a first example, the hot and cold spots correspond to filter regions aligned with and outside of (or proximal the edge of) the light emitter's beam or field angle, respectively. In a second example, the hot and colds spots correspond to the peaks and troughs of the filter pleating, respectively. In a third example, hot and cold spots can correspond to and/or arise from a light source geometry (e.g., shape, size, distance or orientation relative to other filtration system components, etc.), from divergence (or lack thereof) of light from the light source, and/or from other geometric or physical effects. However, hot and cold spots can otherwise be present. These hot and cold spots can lead to inefficient contaminant degradation, inefficient energy utilization (e.g., radiant flux), and/or other negative consequences. Variants of the present invention can reduce and/or remove the presence of hot and cold spots in the irradiance distribution (e.g., normalizing the irradiance across the filter) to generate more uniform irradiance distributions or patterns. For example an optical device (e.g., patterned lens, scattering film, etc.) can be coupled to a light source to generate the more uniform irradiance distribution.

Second, variants of the technology can ensure that all spatial locations of the reactive material are illuminated with at least a threshold optical irradiance. In specific examples, the irradiance distribution corresponding to the optical radiation from the light emitters can be made more uniform and/or even by using an optical device.

Third, variants of the technology can prevent the optical assembly and/or light source from overheating. In specific examples, the thermal management of the light sources can be provided by the fluid (e.g., having fluid in contact with the light emitters), a thermal management system, a support structure with predetermined thermal properties, and/or be otherwise provided. In a second specific example, scattering sites of the optical device can be used and/or disposed to enable efficient thermal transport (e.g., away from the light emitter).

Fourth, variants of the technology can increase the lifetime of the filter (e.g., extend the amount of time that a filter can be used). In specific examples, by redistributing the optical energy, the surface area of the filter can be used more evenly to remove contaminants, thereby decreasing the potential for formation of areas of contaminant agglomeration in the filter. Relatedly, when the filter is approximately uniformly loaded with contaminants, uniform illumination can enable more uniform contaminant degradation over the surface of the filter.

Fifth, variants of the technology can increase the lifetime of a light source (e.g., extend the amount of time that a light source can be used). In specific examples, the use of an optical assembly (e.g., a scattering film) can reduce the intensity of light needed from the light source, leading to a lower operating parameter (e.g., current, voltage, etc. such as relative to a maximum or typical operating parameter) that can used to operate the light source and thereby increasing a lifetime of the light source.

However, variants of the technology can confer any other suitable benefits and/or advantages.

3. System.

The housing 600 preferably functions to enclose one or more components (e.g., flow control mechanism, filter, optical assembly, computing system, sensors, etc.) and generate a working volume separate from an ambient environment surrounding the housing. The housing can additionally or alternatively define (e.g., independent from and/or cooperatively with a flow control mechanism) a fluid flow path through the working environment. The fluid flow path preferably passes from an inlet to an outlet, passing through a filter assembly. However, the fluid flow path can pass over a surface of the filter assembly, and/or otherwise be arranged within the housing. The fluid flow path can pass through the optical assembly or components thereof, pass over (e.g., near a surface of) the optical assembly or components thereof, be isolated from the optical assembly, and/or otherwise be arranged relative to the optical assembly. The fluid flow path is preferably defined by an internal structure of the housing, but can additionally or alternatively be defined cooperatively by the optical assembly, the filter assembly, flow control mechanism, and/or any suitable components.

The housing preferably defines an inlet 610 and an outlet 620, which function to couple the ambient environment to the working environment (e.g., wherein fluid from the ambient environment enters the working environment through the inlet and fluid, preferably purified fluid, exits the working environment to the ambient environment through the outlet). However, the inlet and outlet can be the same and/or can otherwise be arranged. The inlet is preferably arranged proximal a base or bottom of the housing, but can be arranged proximal a top (or cover) of the housing, along a side of the housing, and/or otherwise be arranged within the housing. The outlet is preferably arranged proximal a top or cover of the housing, but can be arranged proximal a bottom (or base) of the housing, along a side of the housing, and/or otherwise be arranged within the housing. The inlet and/or outlet can optionally include flow control structures (such as vanes) that can be used to control a fluid flow direction into or out of the housing (e.g., to increase or decrease a turbulence of air, to facilitate or hinder mixing of air, to modify an air speed, to modify an air direction, etc.).

Interior surfaces of the housing are preferably reflective (e.g., reflect at least 80%, 85%, 90%, 95%, 97.5%, 99%, 99.5%, 99.9%, 100%, values therebetween etc. of optical radiation such as radiation produced by the optical assembly or light source), but can be partially reflective (e.g., reflect between 20-80% of optical radiation) and/or have low reflectance (e.g., reflect at most 20%, 15%, 10%, 5%, 2.5%, 1%, 0%, etc. of optical radiation such as to absorb or otherwise scatter the light).

The housing can include one or more support structures, which function to retain one or more components of the system. The support structures are preferably configured to minimally interfere with the fluid flow path (e.g., to have small profiles, to have curved profiles, to have smooth surfaces, etc.). However, the support structures can be configured in any manner.

The shape of the housing can be determined based on (e.g., match) the form factor of the filter, a form factor of an ambient environment, a target working environment volume, and/or otherwise be determined. In specific examples, the housing can be cylindrical, prismatoid (e.g., polygonal prism), hemispherical, and/or any shape.

The flow control mechanism 300 preferably functions to urge fluid along the fluid flow path. The flow control mechanism can additionally or alternatively function to ensure that the fluid flow path meets target fluid parameters (e.g., laminarity, turbulence, Reynolds number, fluid friction, flow inertia, vorticity, density, flow velocity, pressure, temperature, viscosity, steadiness, etc.). The flow control mechanism can be arranged at (e.g., proximal to, near, adjacent to, etc.) a top, a bottom, a central region, a side, a compartment, an inlet, an outlet, and/or any suitable location(s). The flow control mechanism is preferably arranged downstream relative to a filter (e.g., along the fluid flow). However, the flow control mechanism can be arranged upstream and/or downstream relative to a filter, an optical assembly, a sensor, a computing system, and/or any suitable component(s). In variants, the flow control mechanism can include active and/or passive modules. Examples of active flow control mechanisms can include: fans, blowers, impellers 350, and/or any active flow control mechanisms. Examples of passive flow control mechanisms can include: baffles, flow guides, fan covers, vanes, vents, louvers, and/or any suitable component(s).

The system can include one or more filters 100. The filter(s) preferably functions to trap and/or remove (e.g., destroy) contaminants from the fluid. Each filter can be arranged upstream and/or downstream relative to a flow control mechanism, an optical assembly, a sensor, a computing system, and/or any suitable component(s). At least one filter (e.g., a surface of a filter disposed with active material) is preferably arranged proximal to (e.g., separated from by a predetermined distance such as 1-20 cm) and/or in view of an optical assembly (e.g., light emitters of the optical assembly). However, the filter(s) can be arranged in any suitable manner. Each filter can include one or more layers.

A broad face (e.g., surface) of each filter can be pleated, smooth (e.g., flat), folded, ridged, puckered, curved, a mixture of features, and/or the broad face can have any suitable configuration. Preferably, all of the layers of the filter media have the same broad face configuration; however, each of the layers can have different broad face configurations (e.g., different sizes such as different pleating depth, different configurations, etc.), a subset of the layers can have the same broad face configuration, the layers can have a broad face configuration that depends on adjacent layers (e.g., layer type, layer broad face, layer contaminant removal mechanism, etc.), and/or any other suitable layer broad face configuration can be used.

The pleat count can depend on the size of the filter media. However, the pleat count can be a predetermined value and/or depend on any property(s). The pleat count is preferably between 1-250 pleats such as 3, 5, 10, 20, 35, 50, 60, 75, 90, 105, 125, 150, 175, 200, 225 pleats, and/or values therebetween. However, the pleat count can be greater than 250.

The pleat height (e.g., average peak to trough size of the pleats) is preferably between about 0.1" and 10" such as 0.25", 0.4", 0.5", 1", 1.15", 4", 6", 8", and/or values therebetween. However, the pleat height can be less than 0.1" or greater than 10".

The pleat angle can be any angle between about 0°-180° such as 15°, 30°, 45°, 60°, 75°, 90°, 105°, 120°, 135°, 150°, 165°, and/or values therebetween. However, the angle can additionally or alternatively be between 180-360°, 0-360°, and/or between any suitable range of angles.

The pleat pitch can depend on the pleat count, the pleat height, a target pressure drop across the filter, the pleat angle, the filter and/or layers thereof material, and/or any suitable parameters. The pleat pitch is preferably between about 0.1" and 10" such as 0.25", 0.4", 0.5", 1", 1.15", 2", 4", 6", 8", and/or values therebetween. However, the pleat pitch can be less than 0.1" or greater than 10".

However, a pleated filter 105 can have any suitable geometry.

Examples of layers can include: support materials (e.g., metals, conductive materials, etc.), substrates (e.g., fibrous material, felt, etc.), active materials (e.g., photocatalytic material such as photocatalytic electrochemical oxidation (PECO) material, photocatalytic chemical oxidation (PCO) materials, photoelectrochemical materials, titanium dioxide, zinc oxide, iron oxide, tin oxide, zirconium oxide, cerium oxide, tungsten oxide, vanadium oxide, cadmium sulfide, zinc sulfide, tungsten sulfide, materials as disclosed in U.S. patent application Ser. No. 16/831,354 filed 26 Mar. 2020 titled "SYSTEM AND METHOD FOR PHOTOELECTROCHEMICAL AIR PURIFICATION" and/or U.S. Pat. No. 7,635,450 filed 26 Apr. 2006 titled "PHOTOELECTROCHEMICAL AIR DISINFECTION" each of which is incorporated herein in its entirety by this reference, etc.; chemicals such as acids, bases, solutions, organic compounds, zeolites, metal organic frameworks, etc.; etc.), trapping layers (e.g., mechanical filtration layers, prefilters, MERV-rated materials, HEPA rated filters, etc.), chemical layers, sorptive layers (e.g., absorptive materials, adsorptive materials, etc.), and/or any suitable layers. In variants wherein a filter comprises more than one layer, the layers can be arranged in any order (e.g., relative to the fluid flow). In a specific example, a filter (and/or layer thereof) can include one or more layers (and/or materials) as described in U.S. patent application Ser. No. 16/523,928 filed 26 Jul. 2019 titled "FLUID FILTRATION SYSTEM AND METHOD OF USE" which is herein incorporated in its entirety by this reference.

The active materials are preferably optically activated (e.g., photoactivated), but can be electrically activated, thermally activated (e.g., active at or above a threshold temperature, active at or below a threshold temperature, etc.), mechanically activated, chemically activated, nuclearly activated (e.g., activated by α-, β-, γ-particles), and/or otherwise activated. However, the active materials can be preactivated, not require activation, be activated in the presence of contaminants, and/or be otherwise activated.

Figure 10:
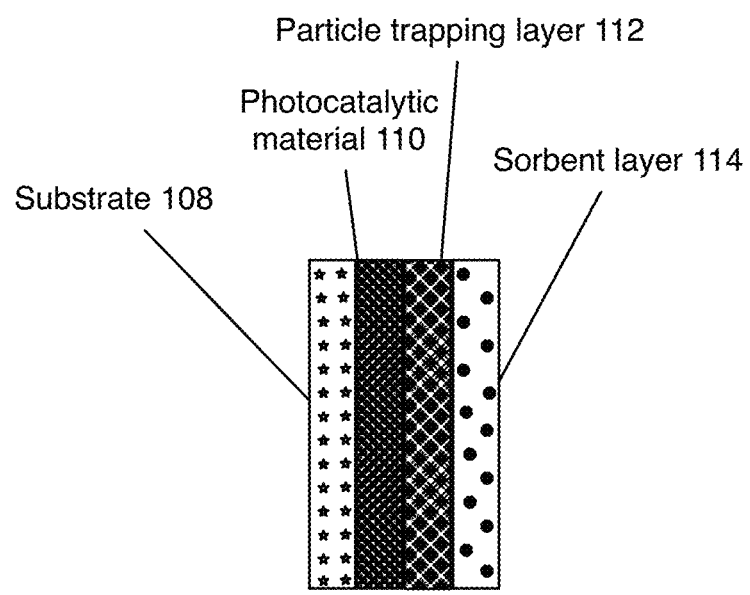
FIG. 10 is an illustrative example of a filter.

In an illustrative example (as shown for instance in FIG. 10), a filter can include: a photocatalytic layer that includes a substrate 108 and photocatalytic material 110 disposed on the substrate (e.g., attached using a binder such as an organic and/or an inorganic binder), a particle trapping layer 112 (e.g., a fibrous layer configured to capture particulates; a layer with a MERV rating that is at least 8, 10, 12, 14, 16, 18, 20, etc.; etc.), a sorbent layer 114 (e.g., a layer configured to sorb one or more contaminant such as VOCs, a layer that includes a scrim and activated carbon disposed on the scrim, etc.). The photocatalytic material is preferably arranged on a surface of the filter proximal the optical assembly, with the remaining layers upstream of the filter (relative to the optical assembly). However, the layers can be arranged in any suitable order.

However, any suitable filter can be used.

The optical assembly 200 preferably functions to activate (e.g., excite, illuminate, prepare for a reaction, etc.) active material of a filter. The optical assembly can additionally or alternatively function to directly or indirectly remove contaminants from the fluid (e.g., by inducing photoreactions; by generating reactive compounds such as hydroxyl radicals, ozone, oxygen radicals, hydrogen radicals, etc.; etc.) and/or perform any suitable function. The optical assembly can be arranged upstream and/or downstream relative to a flow control mechanism, a filter, a sensor, a computing system, and/or any suitable component(s).

The optical assembly is preferably proximal (e.g., near, close, adjacent, etc.) to a filter (e.g., a filter including active material). The active material is preferably in view of (e.g., in line-of-sight of, optically connected to) the optical assembly, but can partially or fully occluded (e.g., a surface of the filter disposed with active material can be distal the optical assembly, a layer of the filter can be arranged between the active layer and the optical assembly, etc.) from the optical assembly. However, the filter and optical assembly can be otherwise arranged. In a specific example as shown in FIGS. 3A and 4A, the filter can have a hollow cylindrical form factor and the optical assembly can be arranged within the filter cavity (e.g., concentrically arranged, non-concentrically arranged, etc.). However, the optical assembly can be arranged around the filter, and/or arranged in any manner.

The optical assembly and/or components thereof are preferably in contact with the fluid flow, but the optical assembly or components thereof can be isolated from the fluid flow (e.g., arranged in a separate compartment of the housing, include a barrier isolating the fluid from the optical assembly, etc.). Variants of the system wherein the optical assembly and/or components thereof are in contact with the fluid flow can provide the benefit of cooling and/or maintaining the temperature of the optical assembly using the fluid (e.g., maintain the temperature below a threshold temperature). However, the optical assembly can additionally or alternatively include a temperature management module (e.g., a heat sink, a thermoelectric cooler, etc.

thermally connected to the ambient environment or other heat sink), not have a temperature control, and/or have any suitable temperature control.

The optical assembly preferably generates optical radiation. The optical radiation preferably defines an intensity distribution 205. The intensity distribution can refer to a total intensity (e.g., an integrated intensity, radiant flux, a nondirectional distribution, etc.), a pointwise intensity, an areal intensity (e.g., at the active material of the filter, at a surface of the filter directed toward or proximal the optical assembly, at a surface a predetermined distance from the optical assembly, etc. such as an irradiance distribution, radiosity distribution, radiance distribution, etc.), a volumetric distribution (e.g., a radiant energy density), an angular distribution (e.g., radiant intensity), and/or refer to any suitable intensity distribution. For example, the intensity distribution can be defined at or relative to a surface of the filter, at a (hypothetical) surface defined a predetermined distance from the optical assembly (with a predetermined geometry), and/or at any suitable reference surface. The intensity distribution can be constant and/or vary in time.

The intensity distribution can depend on a contaminant concentration, a contaminant identity, reaction kinetics, reaction rates, filter lifetime (e.g., target filter lifetime), filter material(s) (e.g., a threshold irradiance or fluence to activate a given active material, a threshold irradiance to control reaction of the photocatalyst and/or reactive species derived therefrom and the filter material, etc.), a flow rate, a pressure drop, a target irradiance, a target contaminant level (e.g., a fraction of contaminants destroyed), a degree of oxidation (e.g., an extent to which a contaminant is degraded), and/or any suitable properties. For example, a minimum irradiance of an irradiance distribution (e.g., at the filter surface) is preferably at least about 10 $W/m^2$ such as 20, 25, 30, 40, 50, 75, 100, 150, 225, 25-100, 10-300 $W/m^2$, or values therebetween. However, the minimum irradiance at the filter can be less than 10 $W/m^2$ and/or greater than 300 $W/m^2$.

The intensity distribution is preferably substantially uniform (e.g., approximately the same intensity at each location of the filter, as shown for example in FIGS. 4A and 4B, less than a predetermined difference between the intensity minima and maxima, a difference in intensity between the maximum intensity and minimum intensity is less than about 1%, 2%, 5%, 10%, 20%, etc.; a difference in irradiance between the maximum irradiance and minimum irradiance is less than about 0.01, 0.1, 0.5, 1, 2, 5, 10, 20, etc. $W/m^2$; standard deviation and/or variance of the intensity is at most about 1%, 2%, 5%, 10%, 20%, 30%, etc. of the mean intensity; etc.), but can be multimodal, patterned (e.g., to match a deposition pattern of material on the filter; to match a filter or layer shape; based on a fluid flow such as based on locations of higher or lower relative flow rates, higher or lower pressure drops, etc.; etc.), monomodal (e.g., normally distributed), be within a predetermined intensity range, and/or be any distribution. However, the intensity of the optical radiation can be random, include hot and/or cold spots, be static, be dynamic (e.g., the irradiance changes over time such as intentionally modulated and/or unintentional changes, etc.) and/or the optical radiation can have any intensity.

The intensity distribution (e.g., at a surface of the filter) is preferably isotropic, but can be anisotropic. In an illustrative example of an anisotropic irradiance distribution, the irradiance can be substantially uniform along a first axis of the filter (e.g., along a longitudinal axis, along a circumference of the filter, etc.) and nonuniform (e.g., varying monotonically, varying periodically, etc.) along a second axis of the filter. For example, an irradiance along a longitudinal axis of the filter surface (e.g., that is parallel to a longitudinal axis of a light source member, to a longitudinal axis of the housing, etc.) can be substantially uniform (e.g., differs by less than 0.1%, 0.5%, 1%, 2%, 5%, 10%, 20%, etc. along the longitudinal axis), and the irradiance along a circumference of the filter surface can be periodic (e.g., with a period matching the pleat count or pleat period). However, any suitable anisotropic intensity distribution can be used.

The intensity distribution preferably does not include dark spots (e.g., locations where the irradiance is less than a threshold irradiance value such as less than 1, 2, 5, 10, 20, 50 $W/m^2$, etc.). In particular intensity distribution preferably does not include dark spots proximal the surface of the filter. However, the intensity distribution can include dark spots and/or otherwise be configured.

Figure 3D:
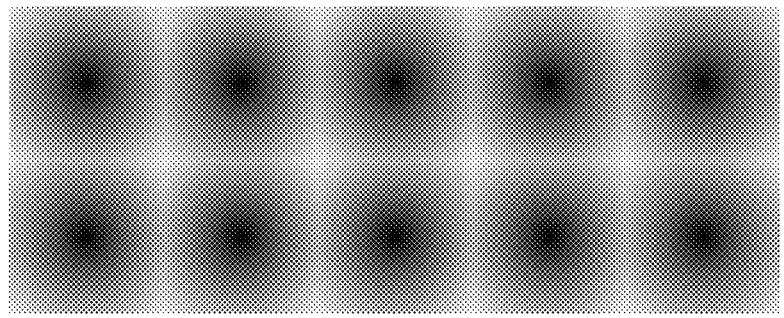
Figure 3D:
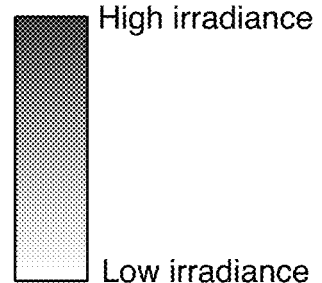
Figure 3E:
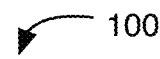
Figure 3E:
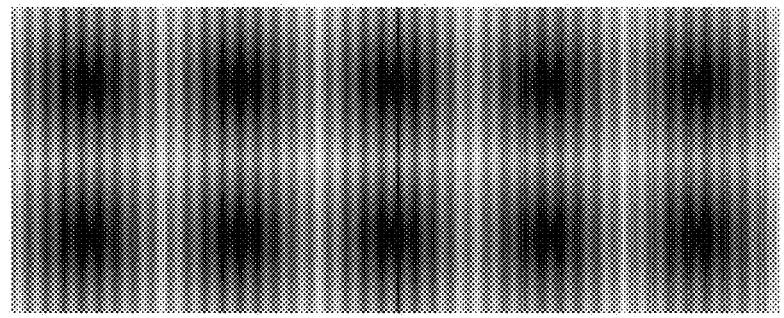

In a first illustrative example (as shown in FIG. 4A or 4B), an irradiance distribution at a surface of a circumscribing cylinder about the optical assembly can be uniform. In a variant of the first illustrative example (as shown in FIG. 4A), light that exits from an optical device (e.g., light from the light source that passes through a scattering film) can be substantially uniform (e.g., in free space). In a second variant of the first illustrative example (as shown in FIG. 4B), light incident on a surface of the filter can be substantially uniform (e.g., vary between a maximum and a minimum by at most 0.1%, 0.5%, 1%, 2%, 5%, 10%, etc.). In a second illustrative example (as shown in FIG. 3C), an irradiance distribution at a surface of a filter can vary between a peak (e.g., portions of the filter closest to the optical assembly) of the filter and a trough (e.g., portions of the filter furthest from the optical assembly) of the filter. The irradiance of the optical radiation proximal the troughs is generally less than the irradiance proximal the peaks (e.g., due to shadowing effects, due to spreading or diffraction of the optical radiation as it propagates a longer distance to reach the trough than the peak, etc.). However, the irradiance of the optical radiation incident on the filter proximal the troughs can be the same as and/or larger than the irradiance of the optical radiation incident on the filter proximal the peaks (e.g., by patterning scattering centers, by attenuating optical radiation at the filter such as using a filter, etc.). In a third illustrative example (as shown in FIG. 3E), when a portion of the filter (such as a particular peak or set of peaks, particular troughs or set of troughs, proximal an edge, proximal a center, etc.) is determined to experience a greater or lesser flow and/or contaminant concentration, the irradiance distribution can be designed based on (e.g., to match) said portion of the filter (e.g., such that the portion of the filter experiencing greater contaminant loading receives greater irradiation, such that a portion of the filter experiencing less contaminant loading receives less irradiation, etc.). The contaminant loading and/or flow rate can be linearly or nonlinearly (e.g., quadratic, cubic, exponentially, logarithmic, sinusoidally, etc.) related to the irradiance distribution. However, the irradiance distribution can have any suitable pattern.

The optical assembly can include: a support structure 230, a light source 250, an optical device 270, and/or any suitable component.

The support structure 230 (e.g., support member) preferably functions to retain the light source and the optical device. The support structure is preferably coupled to (e.g., mounted to) the housing (e.g., inside the housing, inside the working environment defined by the housing, etc.), but can be otherwise arranged. For example, the support structure can be mounted to a pedestal or base of the housing.

However, the support structure can otherwise be mounted. The support structure preferably extends along a longitudinal axis of the housing, but can extend along a transverse axis and/or any suitable axis. The support structure can extend a predetermined distance, a predetermined portion of the housing, and/or otherwise extend into the housing.

The support structure form factor can be cylindrical, hemispherical, planar, hemicylindrical, spherical, prismatoidal (e.g., being shaped like a cuboid, triangular prism, rectangular prism, trapezoidal prism, pentagonal prism, hexagonal prism, heptagonal prism, octagonal prism, prismoid, etc.), toroidal, ellipsoidal, catenoidal, and/or any geometry. The support structure can be absorptive (e.g., absorb greater than about 50% of optical radiation incident on the support structure), reflective (e.g., reflect greater than about 50% of optical radiation incident on the support structure), scattering (e.g., scatter greater than about 50% of optical radiation incident on the support structure), and/or otherwise interact with optical radiation.

In an illustrative example, the support structure is a pentagonal right prism. However the support structure can have any form factor.

The light source 250 preferably functions to generate (and output) electromagnetic radiation 202 (e.g., light, photons, optical radiation, etc.). The electromagnetic radiation preferably includes ultraviolet radiation (e.g., UV-A, UV-B, UV-C, 100-400 nm, 100-280, 100-315, 280-400 nm, 280-315 nm, 315-400 nm, discrete and/or ranges of wavelengths therein, etc.) and/or visible radiation (e.g., 400-800 nm), but can additionally or alternatively include x-rays, infrared, microwave, radio wave, and/or any suitable electromagnetic radiation. The light output by the light source can be diffuse, nondiffuse (e.g., collimated), or have any other suitable optical characteristic.

The light source can include a single light emitter (e.g., a cylindrical light emitter, a volumetric light emitter, a planar light emitter, etc.) and/or a plurality of light emitters (e.g., a plurality of discrete light emitters, a plurality of preferential light emission sites of a light emitter, light emitters arranged with overlapping beam or field angles, etc.). Each light emitter can be the same or different from the other light emitters. Each light emitter can be an extended light emitter, an areal light emitter, a linear light emitter, a point emitter, a volumetric emission LED, a surface emission LED, a masked emission LED, and/or have any suitable geometry. Each light emitter can be a thermal light source (e.g., incandescent light), light emitting diode (e.g., an ultraviolet light emitting diode 255 (UVLED)), gas discharge lamps (e.g., mercury lamps, xenon lamps, etc.), a fluorescent light, a laser, and/or any suitable light emitter.

Figure 2:
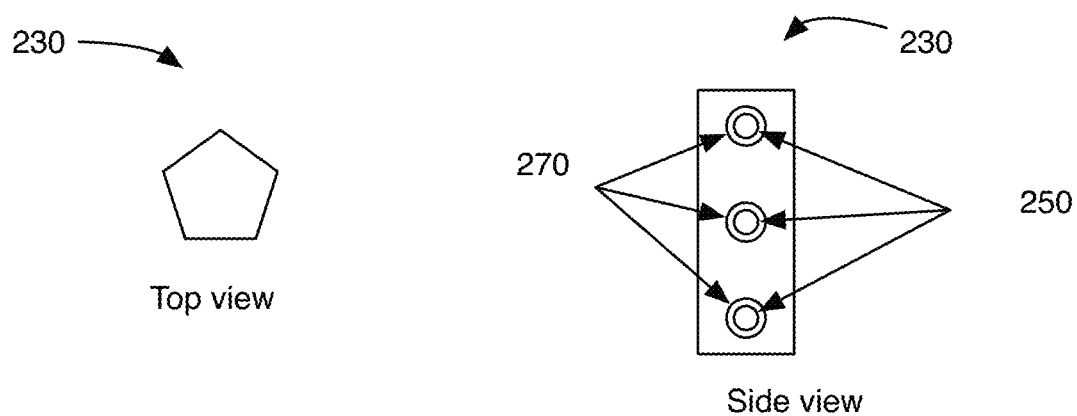
FIG. 2 is a schematic representation of an embodiment of an optical assembly.

In a specific example as shown in FIGS. 2 and 6, each face (e.g., rectangular face, base, etc.) of the support structure can include a plurality of light emitters (e.g., 2 light emitters, 3 light emitters, 5 light emitters, 10 light emitters, 20 light emitters, etc.). Each face preferably has the same number of light emitters, but each face can have a different number of light emitters. The light emitters on each face are preferably level (e.g., at approximately the same height along the support), but can be staggered and/or at any height. The light emitters on each face are preferably evenly distributed (e.g., equal spacing between light emitters, equal spacing between light emitters and housing walls and/or other structures), but can be unevenly distributed. The light emitters can be arranged orthogonal to (e.g., are arranged such that light emitted from the light emitters propagates normal to the support structure) or at another angle to the support structure face.

The light source(s) are preferably separated from the filter by a separation distance. Each light source can have the same separation distance or a different separation distance. The separation distance can refer to the average distance, minimum distance, maximum distance, most common distance, and/or another suitable distance between the filter and the light source. The separation distance is preferably determined based on the target intensity distribution, but can be determined based on a threshold intensity (e.g., a minimum irradiance, a maximum irradiance, an average irradiance, etc.), a fluid flow property (e.g., laminarity, turbidity, flow rate, etc.), an optical device (e.g., based on a focal length, size, scattering distance, light spread, Rayleigh range, and/or other characteristic distance of the optical device or light output therefrom such as a separation distance that is 0.001×, 0.01×, 0.1×, 0.2×, 0.5×, 1×, 2×, 5×, 10×, 100×, 1000×, etc. the characteristic distance of the optical device; based on a divergence angle of the optical radiation; etc.), the housing (e.g., a size of the housing), the filter (e.g., filter size, filter arrangement, filter pleating, filter form factor, relative form factor between the filter and the optical assembly, etc.), light source output, and/or any suitable property. However, the separation distance can be predetermined, variable, and/or otherwise determined. The separation distance is preferably between about 1 and 10 cm (such as 1 cm, 1.5 cm, 2 cm, 3 cm, 5 cm, 6 cm, 7.5 cm, 9 cm, 10 cm, values therebetween). However, the separation distance can be less than 1 cm, greater than 10 cm, and/or any suitable distance.

In general, light output from the light source is non-uniform (e.g., includes dark spots, maxima and minima of the intensity distribution vary by more than 50%, spatially varies, temporally varies, as shown for example in FIGS. 3A-3E, etc.), but can be uniform (for example, the light source can include a mask or otherwise be designed to generate a uniform intensity distribution). This can result (for example when an optical device is not included) in a non-uniform intensity distribution on a surface of the filter. For example, regions of the filter can not be illuminated, can be illuminated with less than a threshold intensity of light (e.g., less than a threshold intensity necessary for photocatalysis), and/or the filter can otherwise be illuminated. The non-uniformity can result from the shape of the light source and/or light emitting element, the position of the light source(s), the dispersion of the light, the divergence of the light, optical elements integrated in the light source (e.g., collimators, diffusers, etc.), and/or the non-uniformity can otherwise occur. However, the light output from the light source can otherwise be distributed.

In an illustrative example (as shown in FIG. 2), a set of LEDs (e.g., UVLEDs) can be mounted to a support member that defines a longitudinal axis and a transverse axis, wherein the set of LEDs are substantially uniformly distributed circumferentially about the support member and are approximately equidistantly distributed along the longitudinal axis.

The optical device 270 preferably functions to modify the light output by the light source (such as by focusing light, collimating light, defocusing light, etc.; modifying the wavelength of the optical radiation; modify the propagation direction of the light; modifying the intensity distribution of the light; etc.), increase or improve a uniformity (e.g., decrease inhomogeneity, decrease a size or number of hot and cold spots, decrease a number or size of dark spots, etc.) of the light output from the light source, and/or can otherwise function. The optical device can additionally or alternatively function to project an image of the light emitter(s) to the filter and/or perform any function. In a specific example, the optical device can include a scattering film (e.g., a film made of optical material that includes one or more scattering sites). The scattering film thickness is preferably between about 100 µm and 1 cm, but can be thinner than 100 µm or thicker than 1 cm.

Light output from the optical device is preferably substantially uniform (e.g., does not include dark spots; a difference between a minimum and a maximum of the intensity is at most 0.01%, 0.02%, 0.05%, 0.1%, 0.2%, 0.5%, 1%, 2%, 5%, 10%, 20%, etc.; spatially uniform; temporally uniform; as shown for example in FIGS. 4A and 4B; etc.), but can be nonuniform. In particular, light that passes through the optical device and is incident on the surface of a filter (e.g., the surface proximal the optical device) is preferably substantially uniform. However, the light can be uniform in free space (e.g., in the fluid within the space between the optical device and the filter), and/or be nonuniform.

The optical device(s) are preferably arranged between the light emitters and the filter, but can be arranged at any suitable location within the system. The optical devices can be mounted to the light source (e.g., the light source support, a separate mounting bracket of the light source, etc.), to the filter, to the housing, and/or otherwise be mounted.

Figure 5B:
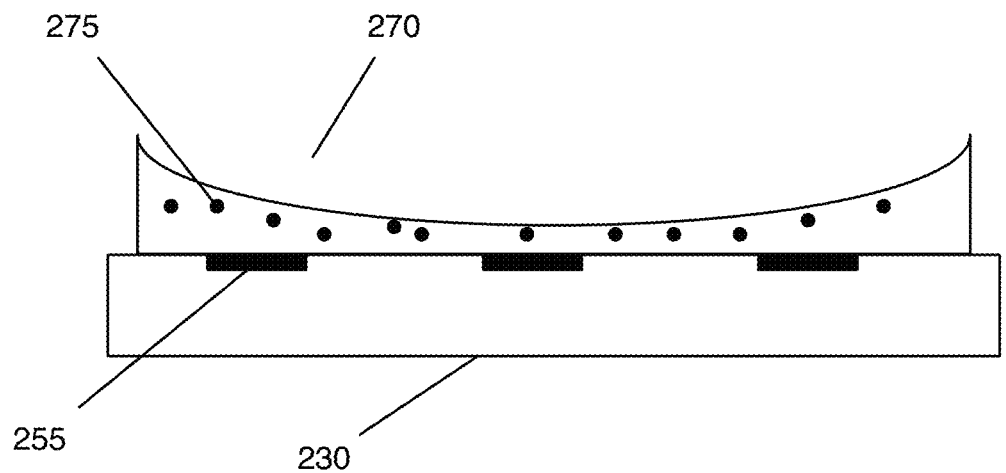
Figure 5C:
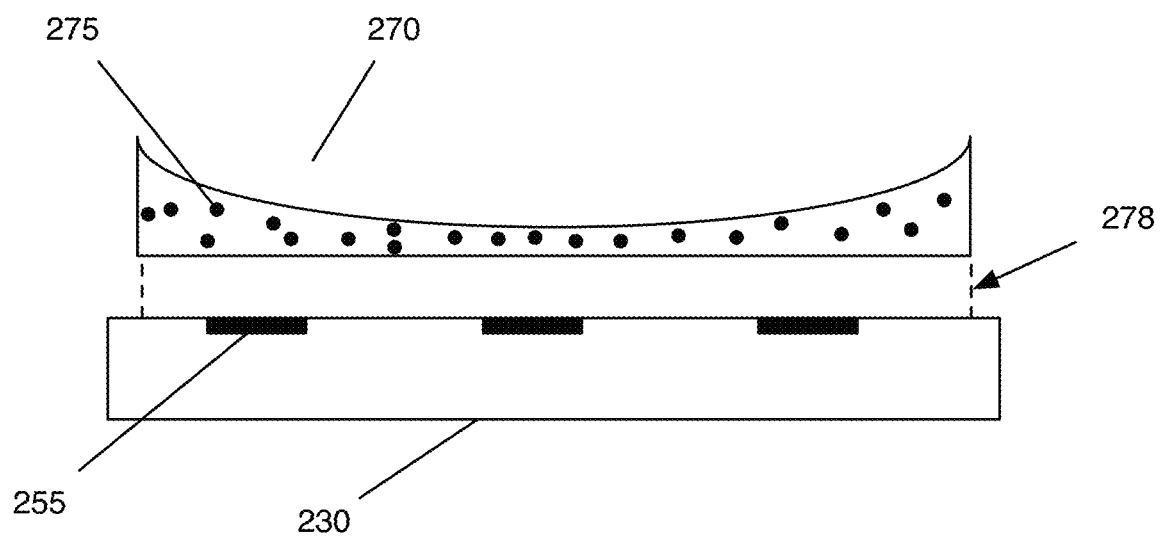

Each light emitter can be associated with (e.g., adjacent to) one or more optical devices. For example, light emitted from a light emitter can interact with (e.g., propagate through) one or more optical device. The optical device can be the same and/or different (e.g., tuned and/or customized based on the properties of the individual light emitter) for each light emitter. In a first example, as shown in FIG. 5A, each light emitter can be associated with a separate optical device. In a second example, as shown in FIG. 5B, each light emitter can be associated with the same optical device (e.g., one optical device per array or light emitter subset; one per support structure, wherein the optical device can function as a light cover; etc.). In a related example, as shown in FIG. 5C, each light emitter the optical device can be separated from the light emitters by a gap. One or more sides of the gap (e.g., upstream, downstream, left, right side, etc.) can be enclosed by a protective structure 278 (e.g., a dust cover, a dust cap, etc.), which can function to prevent dust and/or other particulates from settling on the light emitters and occluding the optical radiation. However, one or more light emitters can be associated with no optical devices and/or can be associated with any suitable optical devices. Additionally or alternatively, the optical device can be part of the filter (e.g., inner filter surface, outer filter surface, coating over the active material, mounted to the filter, etc.)

The optical device material 273 is preferably translucent (e.g., transparent material) to the optical radiation. For example, the optical device material can transmit 50%, 60%, 70%, 75%, 80%, 90%, 95%, 97%, 99%, 99.5%, 99.9%, 100%, 50-100%, less than 50%, and/or any percentage of the optical radiation. The optical device material can include one or more: polymer (e.g., acrylic such as polymethyl methacrylate (PMMA), polystyrene, polycyclic olefins, polyfluoroalkanes, fluorinated ethylene propylene, polydimethylsiloxane, etc.), glass (e.g., quartz, fused silica, silicate, borosilicate, etc.), crystals (e.g., sapphire), birefringent material (e.g., calcite), and/or any suitable material. In an illustrative example, the optical device material can be transparent or translucent to ultraviolet and/or visible radiation (e.g., UV-A, UV-B, UV-C, etc. light with a wavelength between about 100-800 nm, 100-400 nm, 100-280 nm, 280-315 nm, 315-400 nm, 400-800 nm, etc.).

In some variants, the optical device can include a coating. The coating can be an anti-reflection coating (e.g., magnesium fluoride), a protective coating, and/or any suitable coating.

In variants, the optical device can include: diffusers, lenses, frequency shifters (e.g., fluorophores, phosphors, etc.), scattering sites, polarization optics (e.g., polarizers, waveplates, etc.), optical filters (e.g., bandpass filters, short-pass filters, long-pass filters, notch filters, color filters, neutral density filters, etc.), diffractive optics (e.g., gratings), and/or any suitable optics.

The optional lens(es) preferably function to spatially redistribute emitted light and/or to collimate (or partially collimate such as to decrease a divergence angle or) the light. The lens(es) can be plano-concave, plano-convex, biconcave, biconvex, compound, achromatic, prismatic (e.g., regular prismatic), as shown for example in FIGS. 8A-8E, and/or any lens. The lens(es) can be spherical, elliptical, cylindrical, a Fresnel lens (e.g., a biconcave Fresnel lens), aspherical, acylindrical, parabolic, and/or any suitable lens. A focal length of the lens(es) can be any distance between about 0.5-20 cm, can be any distance greater than about 0.5 cm (e.g., have a radius of curvature greater than about 1 cm), can be a distance less than about 0.5 cm, and/or can be any suitable distance. In variants, one or more surface of the optical material can be curved (e.g., concave, convex, sinusoidally, etc.) to form the lens. The curved surface can be proximal, distal, and/or otherwise arranged relative the light source(s). However, the surfaces of the optical material can be planar (e.g., have a random surface structure; have a surface roughness less than about 500 nm, 400 nm, 200 nm, 100 nm, 50 nm, 40 nm, 20 nm, 10 nm, 5 nm, etc.; have a scratch-dig of 60-40, 40-20, 20-10, 10-5, etc.; etc.) and/or have any suitable structure.

The one or more scattering sites 275 preferably function to redirect light propagating through the optical device. Light is preferably redirected from an inhomogeneous direction (e.g., an anisotropic propagation direction) to a more homogeneous direction (e.g., isotropic such as in a cosine squared distribution; superisotropic such as in a cosine to the fourth distribution; anisotropic such as in a predetermined pattern and/or direction; etc.). However, the light can be redirected in any manner and/or direction. The scattering sites can be Rayleigh scatterers, Mie scatterers, intermediate scatterers, fluorescent sites, reflective sites, diffractive sites, and/or can scatter light according to any light scattering property. The scattering sites can be elastic (e.g., do not change or modify a wavelength of light) or inelastic (e.g., change or modify a wavelength of the light) scattering sites. For example, when a spectral density of a light source is not matched to an active material spectrum (e.g., absorption spectrum), inelastic scattering sites can be chosen where the spectrum of the light after inelastic scattering is matched to (or better matched to) the active material spectrum. However, any suitable scattering sites can be used.

The scattering sites can be distributed within the optical material, on a surface of the optical material, within the housing (e.g., to be distributed by fluid flow within the housing, suspended within the housing, etc.), and/or otherwise be located. The scattering sites can be stochastically distributed (e.g., randomly, pseudorandomly, homogeneously, etc.) or nonstochastically distributed (e.g., distributed in a predetermined pattern such as matching a deposition pattern of the active material, matching a filter form factor, matching the filter's peak and trough locations, based on the light emitters, matching a surface of the optical device, etc.; having a greater density of scattering sites at predetermined locations, having different types of scattering sites at predetermined locations, etc.) within the optical device (e.g., within the optical material, on a surface of the optical material, etc.). The scattering sites are preferably distributed through the entire volume of the optical material, but can be distributed on a surface of the optical material (e.g., a surface proximal the light emitters, a surface proximal the filter, etc.), distributed within a portion of the optical material volume (e.g., as shown for example in FIGS. 7A-7E), distributed evenly or unevenly along one or more optical device dimensions (e.g., along the broad face, along the thickness, along the height, etc.), and/or otherwise arranged.

The scattering sites can be nanoscale (e.g., having one or more dimension such as a smallest dimension that is between about 1-100 nm), mesoscale (e.g., having one or more dimension such as a smallest dimension that is between about 100 nm and 1000 nm), microscale (e.g., having one or more dimension such as a smallest dimension that is between about 1 μm and 1000 μm), macroscale (e.g., having one or more dimension such as a smallest dimension that is greater than about 1 mm), picoscale (e.g., less than about 1 nm such as molecular species, clusters, atoms, etc.), and/or be any size.

The concentration of scattering sites can be chosen to generate the intensity distribution, based on a probability of scattering the light, based on a target scattering length (e.g., within the optical material), based on a probability of back scattering, based on a threshold amount of forward scattering, based on a threshold amount of backscattering (e.g., to keep backscattering less than a threshold target such as less than 0.001%, 0.005%, 0.01%, 0.05%, 0.1%, 0.5%, 1%, 2%, 5%, 10%, etc.), can depend on an attenuation coefficient (e.g., a spectral attenuation coefficient, a scattering coefficient, an absorption coefficient, extinction coefficient, etc.) of the scattering sites, and/or can otherwise be chosen. For example, the concentration of scattering sites can be between approximately 1 ppm (part per million) and 20% (e.g., percent by weight, percent by volume, etc.) such as 0.0001%, 0.0002%, 0.0005%, 0.001%, 0.002%, 0.005%, 0.01%, 0.02%, 0.05%, 0.1%, 0.2%, 0.5%, 1%, 2%, 5%, 10%, 15%, 20%, or values therebetween. However, the concentration of scattering sites can be less than 1 ppm or greater than 20%.

The attenuation coefficient of the scattering sites are preferably between about $10^{-5}$ cm$^{-1}$ and $10^5$ cm$^{-1}$ (such as $1\times10^{-5}$, $2\times10^{-5}$, $5\times10^{-5}$, $1\times10^{-4}$, $2\times10^{-4}$, $5\times10^{-4}$, $1\times10^{-3}$, $2\times10^{-3}$, $5\times10^{-3}$, $1\times10^{-2}$, $2\times10^{-2}$, $5\times10^{-2}$, 0.1, 0.2, 0.5, 1, 2, 5, 10, 20, 50, 100, 200, 500, 1000, 2000, 5000, 10000, 20000, 50000, 100000 cm$^{-1}$, or values therebetween). However, the attenuation coefficient can be less than $10^{-5}$ cm$^{-1}$ or greater than $10^5$ cm$^{-1}$. In a specific example, an absorption coefficient of the scattering site can be smaller than a scattering coefficient of the scattering site. However, the absorption coefficient of the scattering site can be the same as and/or larger than the scattering coefficient of the scattering site.

In a first variant, the scattering sites can include one or more nanoparticles. The nanoparticles can be plasmonic nanoparticles, fluorescent nanoparticles (e.g., quantum dots, spectral conversion nanoparticles, etc.), optically scattering nanoparticles, and/or any nanoparticle. The peak of the optical resonance (e.g., plasmon resonance) for each nanoparticle (and/or the collective or average optical resonance for the nanoparticles) is preferably within the wavelength distribution of the optical radiation. For example, when the wavelength of the optical radiation is 380 nm, the nanoparticle optical resonance is approximately 380 nm (e.g., ±1 nm, ±5 nm, ±10 nm, ±20 nm, etc.; such that a full width half maximum of the optical resonance overlaps 380 nm; etc.). However, the nanoparticle optical resonance can otherwise be determined.

Properties of the nanoparticle (e.g., nanoparticle surface chemistry, geometry, material(s), size, etc.) can be selected such that irradiation by the light (e.g., emitted by the light source) induces plasmonic emission, such that an optical resonance of the nanoparticles matches the light, such that an optical resonance of the nanoparticles is tuned to (e.g., matches, overlaps, etc.) the active material, and/or otherwise be selected. However, each nanoparticle can have any suitable optical resonance.

The nanoparticles can be spherical, capsules, rods, sheets, tubes, stars, icosahedral, polyhedral, core-shell, tetrapod, and/or have any geometry.

The nanoparticle size (e.g., average nanoparticle size, maximum nanoparticle size, minimum nanoparticle size, etc.) can depend on the nanoparticle geometry, plasmon resonance (e.g., peak of the plasmon resonance, width of the plasmon resonance, etc.), nanoparticle material(s), and/or any properties. For example, the nanoparticle size (e.g., diameter, effective diameter, characteristic size, etc. such as average size, maximum size, minimum size, modal size, median size, etc.) can be between about 1-100 nm (such as 1 nm, 2 nm, 5 nm, 10 nm, 20 nm, 25 nm, 30 nm, 50 nm, 100 nm etc.), less than 1 nm, greater than 100 nm and/or any suitable size. In an illustrative example, an average size of the nanoparticles is at most about 50 nm.

The nanoparticles are preferably made of a transition metal chalcogenide (e.g., transition metal monochalcogenides such as cadmium sulfide, cadmium selenide, cadmium telluride, zinc sulfide, zinc selenide, zinc telluride, mercury sulfide, mercury selenide, mercury telluride, etc.; transition metal dichalcogenides such as titanium sulfide, titanium selenide, titanium telluride, vanadium sulfide, vanadium selenide, vanadium telluride, molybdenum sulfide, molybdenum selenide, molybdenum telluride, tungsten sulfide, tungsten selenide, tungsten telluride, etc.; transition metal trichalcogenides such as titanium sulfide, titanium selenide, titanium telluride, chromium sulfide, chromium selenide, chromium telluride, vanadium sulfide, vanadium selenide, vanadium telluride, manganese sulfide, manganese selenide, manganese telluride, etc.; transition metal tetrachalcogenides such as vanadium sulfide, vanadium selenide, vanadium telluride, etc.; ternary metal chalcogenides; quaternary metal chalcogenides; etc.) and/or a transition metal oxide (such as zinc oxide, titanium oxide, scandium oxide, vanadium oxide, chromium oxide, manganese oxide, iron oxide, cobalt oxide, nickel oxide, copper oxide, yttrium oxide, zirconium oxide, niobium oxide, molybdenum oxide, ruthenium oxide, rhodium oxide, palladium oxide, silver oxide, cadmium oxide, hafnium oxide, tantalum oxide, tungsten oxide, rhenium oxide, osmium oxide, iridium oxide, platinum oxide, gold oxide, mercury oxide, lanthanide oxides, actinide oxides, etc.). However, the nanoparticles can additionally or alternatively include: one or more metal (e.g., aluminium, gold, silver, chromium, copper, gallium, indium, magnesium, palladium, platinum, rhodium, ruthenium, titanium, tungsten, sodium, lithium, potassium, rubidium, caesium, etc.), semiconductors (e.g., heavily doped semiconductors such as with a carrier concentration exceeding $10^{19}$ cm$^{-3}$; n-doped; p-doped; silicon; silicon-germanium; gallium arsenide; indium phosphide; gallium nitride; etc.), oxides (e.g., transparent conductive oxides such as indium tin oxide, fluorine-doped tin oxide, doped zinc oxide, etc.), nitrides (e.g., transition metal nitrides such as titanium nitride, tantalum nitride, hafnium nitride, zirconium nitride, aluminium nitride, etc.), carbonaceous materials (e.g., carbon nanotubes, graphene, etc.), alloys, and/or any material(s).

Figure 9:
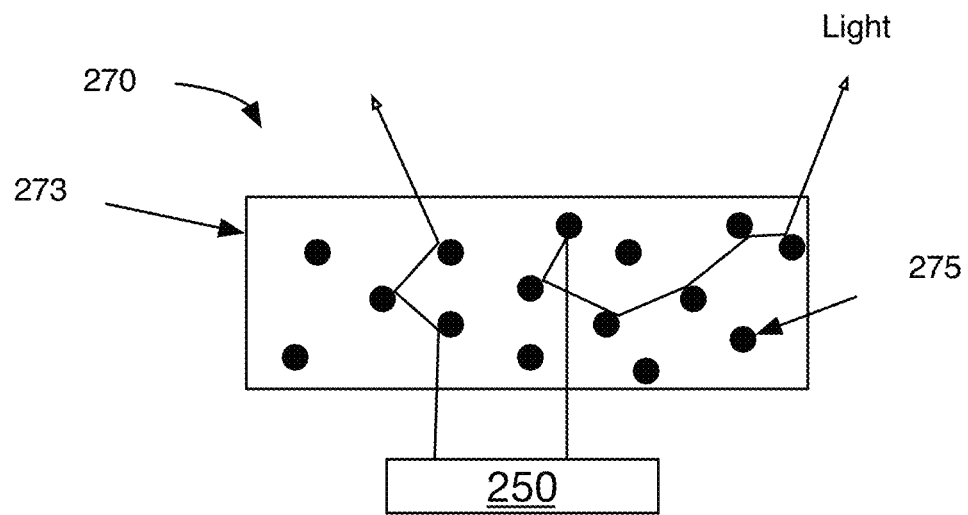
FIG. 9 is a schematic ray tracing diagram for an exemplary light path through a scattering film.

In a second variant, as shown for example in FIG. 9, one or more scattering site can include reflective material (e.g., embedded within the optical device, at a surface of the optical material, at a surface within the optical material, etc.). The reflective material can be nanoparticle, mesoparticle, macroparticle, flake, and/or have any morphology. Examples of reflective material include titanium oxide (e.g., $TiO_2$), aluminium, aluminium oxide, silver, gold, dielectrics, and/or any reflective material.

In a third variant, one or more scattering site can include locations within the optical device with a different index of refraction. For example, the scattering sites can correspond to regions of the optical device with different densities, with different materials (e.g., transparent materials each with different indices of refraction), with different sized and/or shaped regions (e.g., each scattering site comprises an irregular shape such as a pointed shape that can promote refraction of light in multiple directions, a plurality of spherical sites with differing sizes and/or differing indices of refraction, etc.), and/or be otherwise arranged. In an illustrative example, each scattering site can correspond to a glass beads, wherein plurality of glass beads can correspond to a broad size distribution and/or to a plurality of materials.

In a fourth variant, one or more scattering site can include a luminescent material. In this variant, the stokes shift of the luminescent material is preferably small (e.g., less than about 5 nm, 10 nm, 20 nm, 30 nm, etc.), but can be large (e.g., greater than about 30 nm, 50 nm, 100 nm, etc.) and/or any suitable value. The luminescent material preferably absorbs the optical radiation emitted by the light emitters. The luminescent material preferably emits optical radiation that matches (e.g., is tuned to) the optical resonance(s) of the active material. The luminescent material can be disposed as a thin film, a thick film, a nanoparticle, a molecule, and/or in any manner. In specific examples, the luminescent material can include: quantum dots (e.g., semiconductor quantum dots, perovskite quantum dots, etc.), lanthanide doped materials (e.g., lanthanum, cerium, praseodymium, neodymium, promethium, samarium, europium, gadolinium, terbium, dysprosium, holmium, erbium, thulium, ytterbium, lutetium, yttrium, and/or scandium doped materials), coumarin and/or coumarin derivatives (e.g., hydroxycoumarin, methoxycoumarin, etc.), and/or any luminescent material.

In a fifth variant, the scattering sites can include surface features of the optical device. For example, the surface of the optical device can be roughened (such as by sand blasting, surface polishing, grinding, etc. the optical device) such that the roughened surface scatters the optical radiation.

In a sixth variant, the scattering sites can include defects in the optical device (and/or coating of the optical device). For example, defects can include: cracks, point defects, line defects, planar defects, bulk defects (e.g., pores, cracks, inclusions, etc.), precipitates, and/or any defect.

In a seventh variant, the scattering sites can include a combination of scattering sites from the first through sixth variants described above.

However, any scattering site can be used.

In some embodiments, the optical device preferably has a high thermal conductivity, which can function to control (and/or maintain) a temperature of the light emitters at, below, and/or above a threshold temperature and/or decrease heating of the optical device (e.g., from absorption of light).

For example, a scattering film can be configured to remove heat from a light source (e.g., during operation of the light source). In these embodiments, the optical device is thermally coupled to and/or in thermal contact with the light sources, but can be otherwise configured. The thermal conductivity is preferably at least about 0.5 W/(m K) such as 0.75, 1, 2, 3, 5, 10, 20, 50, 100, 200, 500, 1000, 2000, 5000, greater than 5000, 5-20, 1-10, 10-50, 25-200, 100-5000 W/(m*K), etc. However, the thermal conductivity of the optical device can be low (e.g., less than about 0.5 W/(m*K)). The thermal conductivity can be a property of the optical device material, a property of the geometry and/or structure of the optical device, a property of the scattering sites (e.g., material, concentration of scattering sites, density of scattering sites, etc.), conferred and/or modified by the scattering sites, and/or be otherwise determined.

The optional computing system 400 preferably functions to control the operation of the system and/or determine one or more fluid flow parameter based on the sensor data. Examples of system operation parameters include: system (and/or component) temperature, flow control mechanism rate (e.g., impeller speed), illumination intensity (e.g., a minimum irradiance of the irradiance distribution, an average irradiance of the irradiance distribution, etc.), noise level, operation mode (e.g., targeted operation modes based on contaminants), and/or any operation parameter. The computing system can be coupled to (e.g., in communication with) the sensors 500 (e.g., VOC sensors, particulate sensors, etc.), the housing, the optical assembly, the filter, and/or any suitable component. The computing system can be local, remote (e.g., a server, cloud computing, etc.), and/or distributed (e.g., between a local computing system and a remote computing system).

In some variations, the computing system and/or other suitable component can determine a filter orientation (e.g., rotation, arrangement such as relative to the light source, pleat locations, etc.) and adjust the light source operation (e.g., intensity of the light source, scattering sites, etc.) based on the filter orientation. These variations can function to improve a uniformity of the intensity distribution at the filter, increase an intensity distribution (e.g., a maximum, minimum, average of the intensity distribution such as at a trough or valley of a pleated filter, at a peak of a pleated filter, etc.), and/or can otherwise function. For example, the filter orientation can be measured (e.g., using a sensor, using an NFC device, optically, etc.), estimated, predetermined (e.g., based on a filter or housing loading guide), and/or otherwise be determined. Examples of adjusting the light source operation can include: increasing a current or voltage applied to the light source (e.g., driving the light source to output more light), adjusting an orientation of the filter relative to the light source (e.g., aligning a filter to a scattering site pattern), adjusting the scattering sites (e.g., applying a current to align or change an alignment of scattering sites, applying energy such as electrical or thermal energy to change a scattering coefficient of the scattering sites, etc.), and/or otherwise adjusting an operation parameter of the light source and/or filtration system.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the preferred embodiments of the invention without departing from the scope of this invention defined in the following claims.

We claim:

1. An air purification system comprising:
    a housing defining an inlet, an outlet, and an air flow path between the inlet and the outlet;
    an impeller configured to urge air along the air flow path;
    a pleated filter intersecting the air flow path, the pleated filter comprising a substrate with photocatalytic material disposed on a first surface of the substrate and a metal mesh electrically connected to the photocatalytic material; and
    a light source member comprising:
        a polygonal prismatic support;
        a set of ultraviolet light emitting diodes (UVLEDs) on each rectangular face of the polygonal prismatic support, wherein the sets of UVLEDs are directed toward the first surface of the substrate, wherein the sets of UVLEDs are approximately equidistantly spaced along a longitudinal axis between a first and second base of the polygonal prismatic support; and
        a UV transparent material loaded with UV scattering nanoparticles, wherein the UV transparent material is arranged between the UVLEDs and the pleated filter, wherein the UV scattering nanoparticles are configured to scatter light emitted by the UVLEDs.

2. The air purification system of claim 1, wherein a pleat depth of the pleated filter is between about 1 and 5 cm.

3. The air purification system of claim 1, wherein a scattering spectrum of the light scattered by the nanoparticles matches an absorption spectrum of the photocatalytic material.

4. The air purification system of claim 1, wherein the UV scattering nanoparticles comprise a transition metal chalcogenide or a transition metal oxide.

5. The air purification system of claim 1, wherein an irradiance of the scattered light proximal a trough of the pleated filter is configured to differ from an irradiance of the scatter light proximal a peak of the pleated filter by at most 30%.

6. The air purification system of claim 1, wherein an irradiance of light along a longitudinal axis of the pleated filter, parallel to the longitudinal axis of the light source member, is configured to be substantially constant.

* * * * *